US010603483B2

(12) United States Patent
Seifert et al.

(10) Patent No.: US 10,603,483 B2
(45) Date of Patent: Mar. 31, 2020

(54) LEAD IMPLANT FIXATION MECHANISM

(71) Applicant: Medtronic, Inc., Minneapolis, MN (US)

(72) Inventors: Kevin R. Seifert, Forest Lake, MN (US); Maggie J. Pistella, Minneapolis, MN (US); Thomas D. Brostrom, Wayzata, MN (US); Keith D. Anderson, Minneapolis, MN (US); Gareth Morgan, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 283 days.

(21) Appl. No.: 15/496,270

(22) Filed: Apr. 25, 2017

(65) Prior Publication Data
US 2017/0312494 A1 Nov. 2, 2017

Related U.S. Application Data

(60) Provisional application No. 62/328,771, filed on Apr. 28, 2016.

(51) Int. Cl.
*A61N 1/05* (2006.01)

(52) U.S. Cl.
CPC .............. *A61N 1/05* (2013.01); *A61N 1/0504* (2013.01); *A61N 1/059* (2013.01); *A61N 1/0563* (2013.01); *A61N 2001/0582* (2013.01)

(58) Field of Classification Search
CPC ........... A61N 1/059; A61N 2001/0582; A61M 2025/0293
See application file for complete search history.

(56) References Cited

U.S. PATENT DOCUMENTS

| | | | |
|---|---|---|---|
| 4,437,475 | A | 3/1984 | White |
| 4,553,961 | A | 11/1985 | Pohndorf et al. |
| 4,672,979 | A | 6/1987 | Pohndorf |
| 5,242,431 | A | 9/1993 | Kristiansen |

(Continued)

OTHER PUBLICATIONS

(PCT/US2017/029535) PCT Notification of Transmittal of the International Search Report and the Written Opinion of the International Searching Authority, dated Jun. 29, 2017, 12 pages.

*Primary Examiner* — George R Evanisko (57) ABSTRACT

A fixation mechanism of an implantable lead includes a plurality of depressions of an outermost surface of the lead and a relatively flexible sleeve mounted around the outermost surface. The depressions are spaced apart from one another along a length, and each extends circumferentially, wherein a longitudinal center-to-center spacing between each adjacent depression is uniform along the length, and each depression is of substantially the same size. The sleeve has an internal surface in sliding engagement with the outermost surface of the lead, and an external surface, in which suture grooves are formed. A longitudinal center-to-center spacing between adjacent suture grooves may be substantially the same as, or a multiple of, the longitudinal center-to-center spacing between adjacent depressions of the outermost surface of the lead. The sleeve may also include a ridge protruding from the internal surface, aligned with, or offset (by center-to-center spacing of depressions) from, the grooves.

23 Claims, 8 Drawing Sheets

(56) References Cited

U.S. PATENT DOCUMENTS

| | | | |
|---|---|---|---|
| 5,423,763 A | 6/1995 | Helland et al. | |
| 5,476,493 A | 12/1995 | Muff | |
| 5,584,874 A | 12/1996 | Rugland et al. | |
| 5,628,780 A | 5/1997 | Helland et al. | |
| 5,746,722 A | 5/1998 | Pohndorf et al. | |
| 5,824,032 A | 10/1998 | Belden | |
| 7,082,337 B2 | 7/2006 | Sommer et al. | |
| 7,158,838 B2 | 1/2007 | Seifert et al. | |
| 7,283,878 B2 | 10/2007 | Brostrom et al. | |
| 8,000,811 B2 | 8/2011 | Hill | |
| 8,126,569 B2 | 2/2012 | Rivard et al. | |
| 8,249,720 B2 | 8/2012 | Verzal et al. | |
| 8,271,096 B2 | 9/2012 | Rivard et al. | |
| 8,532,789 B2 | 9/2013 | Smits | |
| 8,649,881 B2 | 2/2014 | Helgesson | |
| 8,958,891 B2 | 2/2015 | Kane et al. | |
| 2008/0228251 A1* | 9/2008 | Hill | A61M 25/02 607/126 |
| 2009/0125058 A1 | 5/2009 | Bodner et al. | |
| 2009/0125059 A1 | 5/2009 | Verzal et al. | |
| 2010/0324569 A1 | 12/2010 | Helgesson | |
| 2013/0158640 A1 | 6/2013 | Soltis et al. | |
| 2015/0306374 A1 | 10/2015 | Seifert et al. | |
| 2016/0157890 A1 | 6/2016 | Drake et al. | |
| 2016/0158530 A1 | 6/2016 | Drake et al. | |
| 2016/0158567 A1 | 6/2016 | Marshall et al. | |
| 2016/0175008 A1 | 6/2016 | Seifert et al. | |

\* cited by examiner

LEAD IMPLANT FIXATION MECHANISM

RELATED APPLICATIONS

This application claims the benefit of the filing date of a provisional U.S. Application Ser. No. 62/328,771, filed Apr. 28, 2016, the content of which is incorporated by reference herein its entirety.

FIELD OF THE DISCLOSURE

The present disclosure pertains to implantable medical devices, and more particularly to fixation mechanisms for medical electrical leads.

BACKGROUND

Implantable medical electrical systems known in the art may include a pulse generator device and one or more electrodes that deliver electrical pulses from the device to a target site within a patient's body. Such an electrode is typically part of an elongate implantable medical electrical lead. An elongate conductor carried in an insulation body of the lead may electrically couple the electrode to a proximal connector of the lead, which is configured to plug into the device for electrical coupling thereto. When the connector is plugged into the device, which is implanted in a superficial subcutaneous pocket of the patient, and the electrode is positioned in close proximity to the target site, a length of the insulation body between the connector and the electrode is often fixed, or anchored to tissue to prevent dislodgement of the positioned electrode.

BRIEF DESCRIPTION OF THE DRAWINGS

The following drawings are illustrative of particular embodiments of the present disclosure and therefore do not limit the scope of the description. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of disclosed embodiments. Rather, the following description provides practical examples, and those skilled in the art will recognize that some of the examples may have suitable alternatives.

Figure 1:
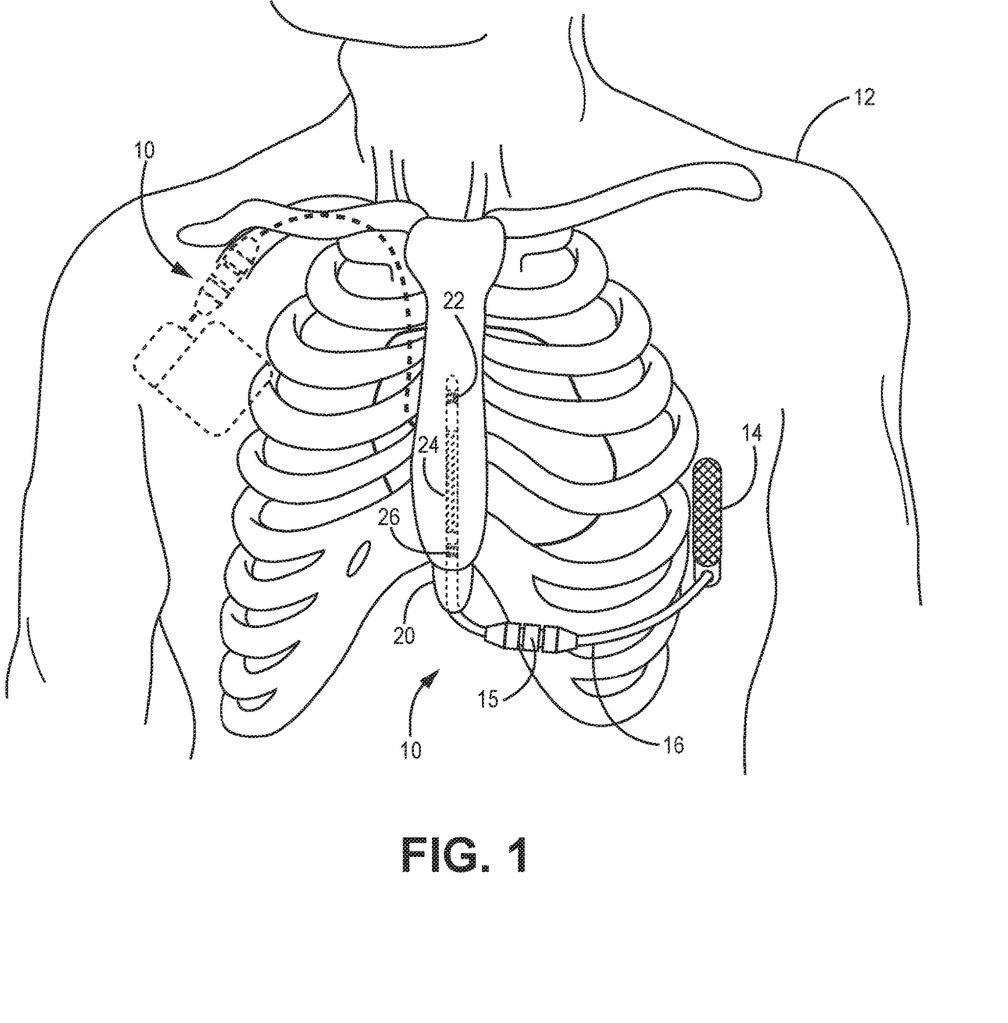
FIG. 1 is a schematic showing an exemplary implanted medical electrical system.

FIG. 1 is a schematic showing an exemplary extracardiovascular medical electrical system 10 that includes a pulse generator 14 and an implantable medical electrical lead 16 coupled thereto. Pulse generator 14 is shown implanted subcutaneously on the left mid-axillary of a patient 12, superficially of the patient's ribcage. Pulse generator 14 is configured to provide cardiac stimulation therapy (e.g., defibrillation, cardioversion, and/or pacing), and pulse generator 14 may include a hermetically sealed housing in which the appropriate electronics and a power supply are contained. The housing may be formed from a conductive material, such as titanium, or from a combination of conductive and non-conductive materials. Pulse generator 14 further includes a connector module by which lead 16 is electrically coupled to the electronics contained therein, for example, by electrical contacts contained within the module and a corresponding hermetically sealed feedthrough assembly, such as is known in the art. The conductive material of the device housing may be employed as an electrode, for example, to provide the aforementioned therapy in conjunction with one of pacing electrodes 22 or 26 and/or a defibrillation electrode 24 of lead 16, the distal portion of which is shown implanted intrathoracically in a sub-sternal space, e.g., within the loose connective tissue and/or sub-sternal musculature of the anterior mediastinum. The distal portion of lead 16 may be implanted extrathoracically (e.g., within the subcutaneous tissue and/or muscle), transvenously, epicardially, pericardially or in other locations within patient 12.

FIG. 1 illustrates a sleeve 15 mounted around lead 16, wherein sleeve 15 is configured to receive sutures thereabout in order to anchor, or fix lead 16 to subcutaneous muscle fascia that overlays the ribcage. However, such an implant configuration may require more holding force, than that achieved with this traditional fixation, in order to prevent movement of the distal portion of lead 16 carrying electrodes 22, 24 and 26. Embodiments of implantable medical electrical lead fixation mechanisms disclosed herein are configured to enhance lead fixation/anchoring for this implant configuration, but may be employed in other implant configurations, for example, a pectoral and transvenous implant configuration 10' shown with dashed lines in FIG. 1, purely subcutaneous implant or other configuration.

Figure 2A:
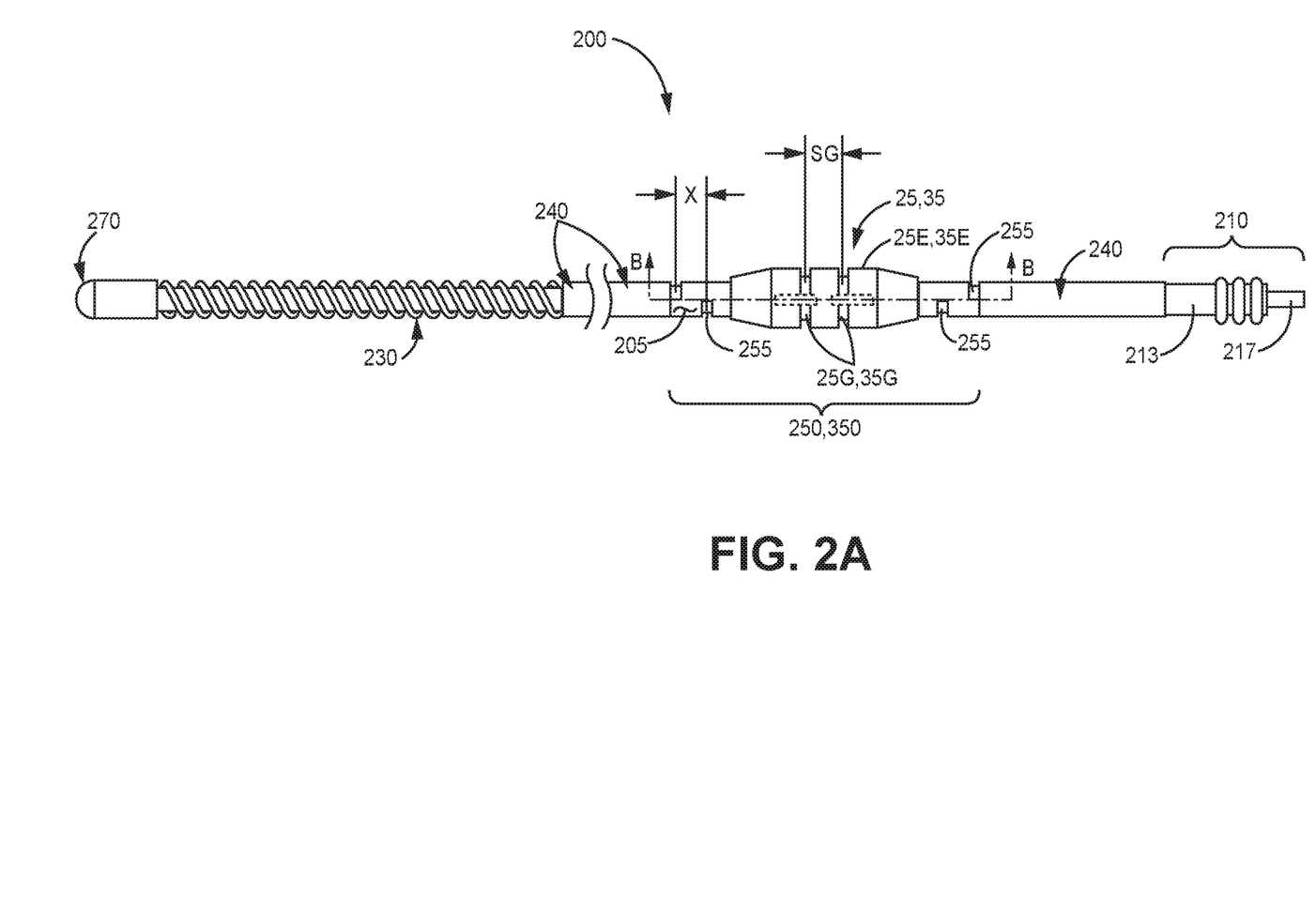
FIG. 2A is a plan view of an implantable medical electrical lead, according to some embodiments.

FIG. 2A is a plan view of an implantable medical electrical lead 200, according to some embodiments. FIG. 2A illustrates lead 200 including a connector 210, a high voltage electrode 230 (e.g., for cardiac defibrillation), and a low voltage electrode 270 (e.g., for cardiac pacing and/or sensing). Any suitable electrode and connector construction known to those skilled in the art may be employed. FIG. 2A further illustrates an elongate insulation body 240 of lead 200 extending between connector 210 and electrodes 230, 270. Body 240 may be formed by a multi-lumen tube (e.g., extruded medical grade polyurethane or silicone rubber, or a combination thereof), and a conductor for each electrode 230, 270 may extend in a respective lumen thereof (e.g., conductor 260 show in FIG. 2B), wherein each conductor electrically couples a corresponding electrode 230, 270 to a corresponding electrical contact 213, 217 of connector 210. Any suitable conductor construction known to those skilled in the art may be employed. With further reference to FIG. 2A, a fixation mechanism 250, 350 of lead 200 is shown including an outermost surface 205 of lead 200, which overlays insulation body 240, and a relatively flexible sleeve 25, 35 mounted around outermost surface 205. An internal surface 25I, 35I of sleeve 25, 35 (shown in FIGS. 2B-3) is in sliding engagement with outermost surface 205.

According to the illustrated embodiment, outermost surface 205 of fixation mechanism 250, 350 includes a plurality of depressions 255 spaced apart from one another along a length of a portion of the body 240 (e.g., about four inches), wherein each depression 255 extends circumferentially around body 240, and each depression 255 is of substantially the same size. However, in some embodiments, the outermost surface 205 may include a single depression. Sleeve 25, 35 of fixation mechanism 250, 350 includes at least two suture grooves 25G, 35G formed in an external surface 25E, 35E thereof. FIG. 2A illustrates a longitudinal center-to-center spacing SG between adjacent suture grooves 25G, 35G, and a longitudinal center-to-center spacing X between adjacent depressions 255. According to some preferred embodiments, spacing X is uniform along the length of body 240, and spacing SG is substantially the same as spacing X, or a multiple thereof. Spacing X may be approximately 0.15 inch, in some embodiments. According to those embodiments of lead 200 intended for implant in an extravascular tunnel (e.g., substernal or subcutaneous tunnel), for example, as shown in FIG. 1, the fixation mechanism 250, 350 may be located along body 240 to secure lead in relatively close proximity to an incision made near the xiphoid process 20.

Figure 2B:
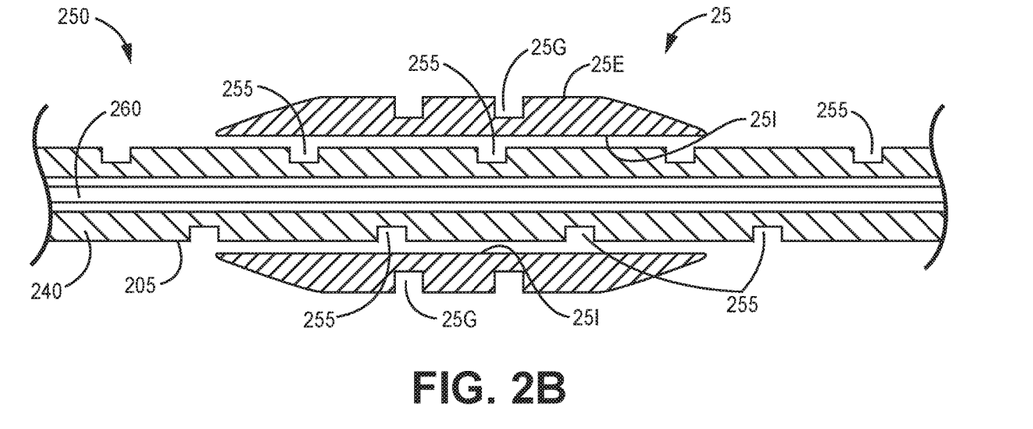
FIG. 2B is a cross-section view through section line B-B of FIG. 2A, according to some embodiments.
Figure 2C:
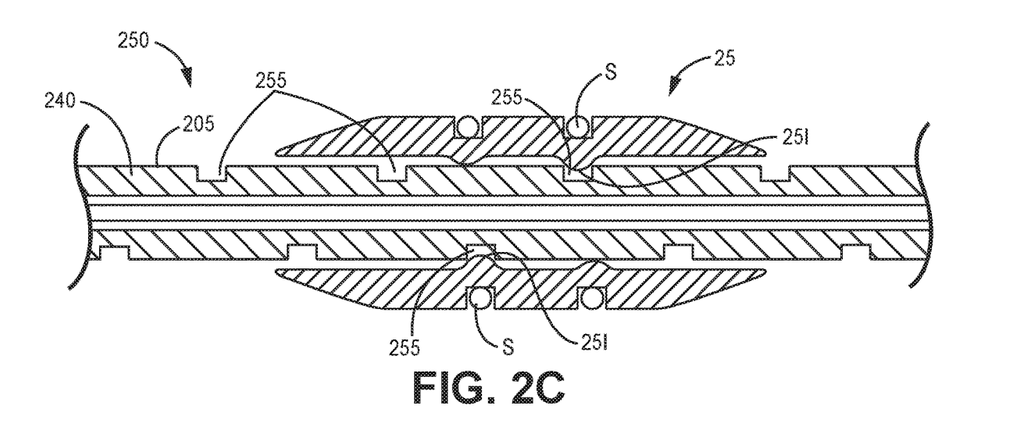
FIG. 2C is another cross-section view through section line B-B, according to some embodiments.

FIG. 2B is a cross-section view through section line B-B of FIG. 2A, according to some embodiments of fixation mechanism 250. FIG. 2B illustrates sleeve 25 positioned so that each suture groove 25G of sleeve 25 is aligned with a depression 255 of outermost surface 205, as facilitated by the aforementioned uniform spacing SG that corresponds to uniform spacing X. FIG. 2C is another cross-section view through the same section line, but showing fixation mechanism 250 employed. FIG. 2C illustrates a suture S extending in each groove 25G and tightened down to deform sleeve 25 into interlocking engagement with the underlying depressions 255. This interlocking engagement may enhance the holding force of sleeve 25 around lead 200. With reference back to FIG. 2A, according to some embodiments and methods, when suture sleeve 25 includes one or more slots extending through the sidewall thereof (shown with dashed lines), an operator may visualize depressions 255 beneath sleeve 25 when positioning sleeve 25 along outermost surface 205 so that grooves 25G of sleeve 25 are aligned with depressions 255 prior to suturing.

Figure 3:
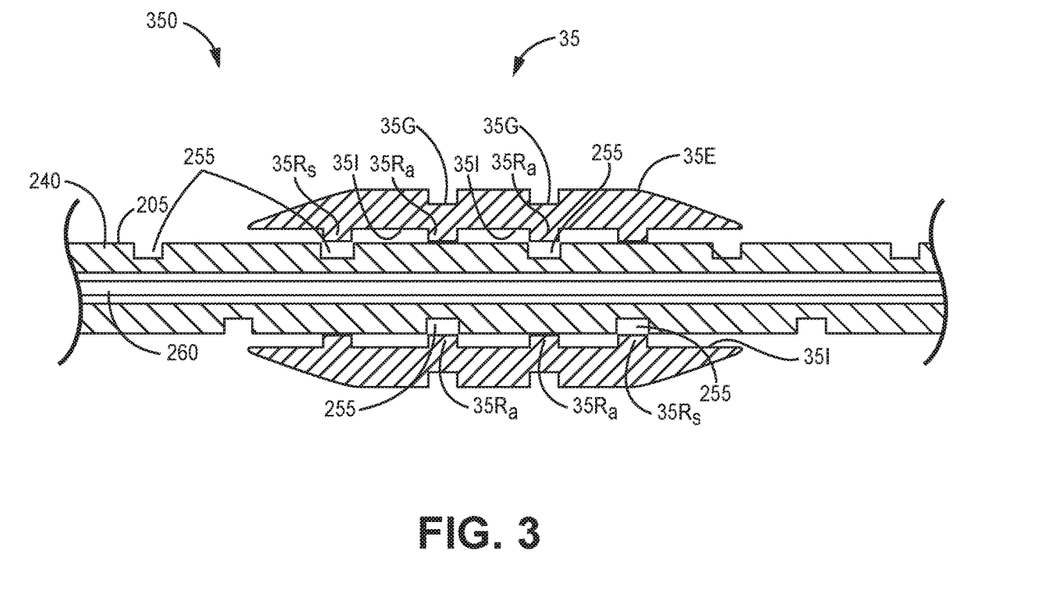
FIG. 3 is a cross-section view of a fixation mechanism, according to some alternate embodiments.

FIG. 3 is a cross-section view through fixation mechanism 350, which includes suture sleeve 35, according to some alternate embodiments. FIG. 3 illustrates sleeve 35 including one or more ridges $35R_a$ protruding from inner surface 35I, wherein each ridge $35R_a$ is longitudinally aligned with a corresponding suture groove 35G, and each is sized to fit within a depression 255 of outermost surface 205. Thus, it may be appreciated that, when sutures are tightened around sleeve 35, in grooves 35G, each underlying ridge $35R_a$ is forced into interlocking engagement with the corresponding depression 255, which may greatly enhance a holding force of sleeve 35 around lead 200. FIG. 3 further illustrates one or more offset ridges $35R_s$, which are optional, protruding from inner surface 35I and longitudinally spaced apart from suture grooves 35G. If one or more offset ridges $35R_s$ are included, a spacing between each offset ridge $35R_s$ and the closest suture groove 35G preferably corresponds to spacing SG (FIG. 2A), so that, when sleeve 35 is positioned along outermost surface 205 with each ridge $35R_a$ longitudinally aligned with a corresponding depression 255, each offset ridge $35R_s$ is also longitudinally aligned with a corresponding depression 255, for example, to interlock therewith when sutures are tightened around sleeve 35. As described above, optional slots (dashed lines, FIG. 2A) through the sidewall of sleeve 35 may enable an operator to visualize underlying depressions 255 for the proper positioning of sleeve 35 along outermost surface 205. However, a tactile feedback of ridges $35R_a$, $35R_s$ moving over depressions 255 may assist the operator in properly positioning sleeve 35. Furthermore, an offset ridge 35R included in sleeve 25 can provide some tactile feedback for positioning sleeve 25 along outermost surface 205. With reference back to FIGS. 2B-C, sleeve 25, in some alternate embodiments, may include one or more offset ridges $35R_s$, for example, one longitudinally spaced apart from suture grooves 25G, on either side thereof, to be longitudinally aligned with a corresponding depression 255 when each groove 25G is aligned with a corresponding depression.

Figure 4A:
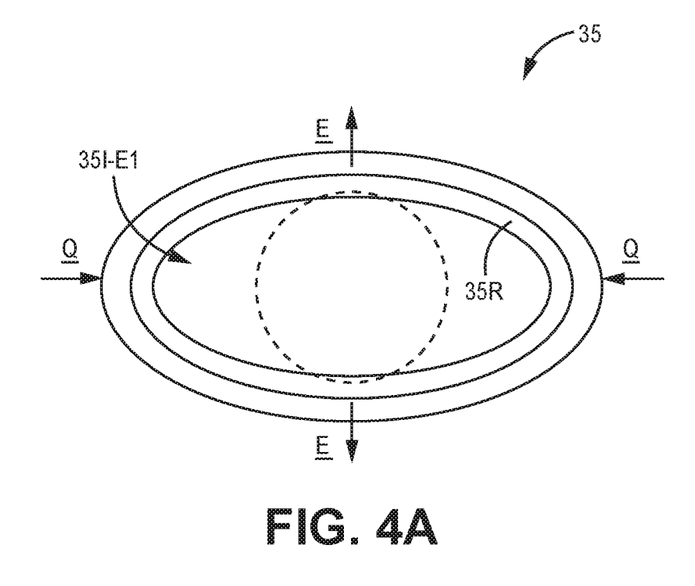
FIGS. 4A-B are end views showing profiles for alternative sleeve embodiments.

According to some exemplary embodiments, sleeve 25, 35 is molded from medical grade silicone rubber, which may include a radiopaque filler blended therewith. Internal surface 25I, 35I of sleeve 25, 35 may define a generally round, circular profile, that corresponds to a generally round, circular profile of outermost surface 205 of lead. But, with reference to the end view of FIG. 4A, sleeve 35 is shown having a generally elliptically shaped inner profile 35I-E1, according to some embodiments. Ridge(s) 35R of sleeve 35 interlock with each depression 255 of outermost surface 205, which is represented with a dashed line in FIG. 4A, when inner profile 35I-E1 is un-deformed. Then, to slide sleeve 35 along outermost surface 205, the operator may squeeze sides of sleeve 35, per arrows Q, so that profile 35I-E1 expands per arrows E and ridge(s) 35R disengage from depression(s) 255.

Figure 4B:
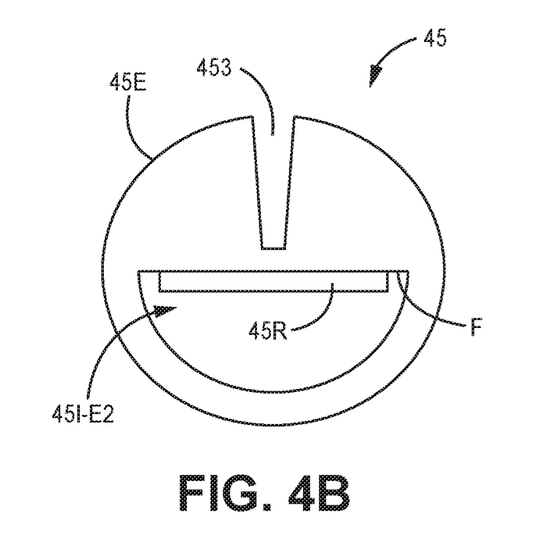

FIG. 4B is an end view of a suture sleeve 45 that has a generally elliptically shaped inner profile 45I-E2 of another configuration. FIG. 4B illustrates inner profile 45I-E2 including a flat aspect F, from which one or more ridges 45R protrude. Sleeve 45 may also be formed from medical grade silicone rubber. FIG. 4B further illustrates a relief 453 formed in an external surface 45E of sleeve 45. According to the illustrated embodiment, each ridge 45R, like each ridge 35R, is sized to fit within each depression 255 of outermost surface 205 of lead 200. Thus, when a suture is tightened around sleeve 45, relief 453 allows the sidewall of sleeve 45 to flex so that each ridge 35R comes into interlocking engagement with the corresponding depression to enhance a holding force of sleeve 45 around lead 200.

Figure 5:
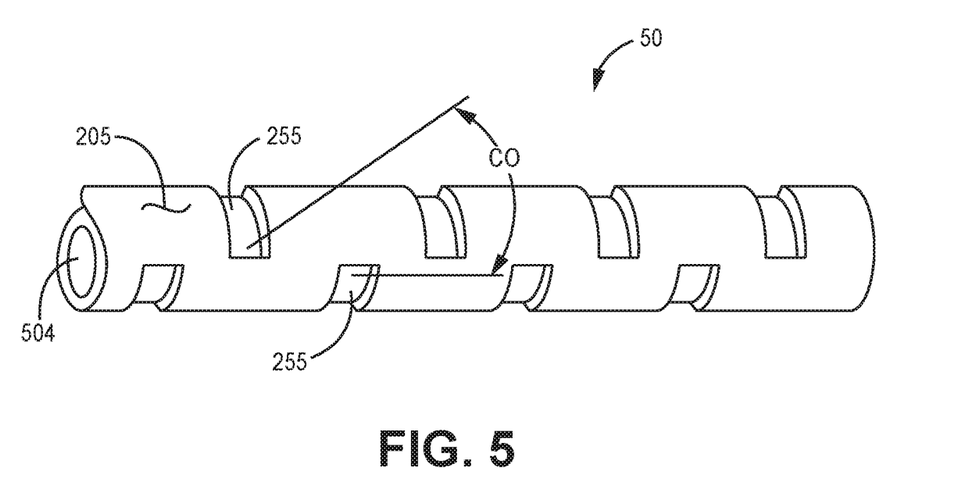
FIG. 5 is a perspective view of a portion of a fixation mechanism, according to some embodiments.

With reference back to FIGS. 2B-3, outermost surface 205 is shown being integral with insulation body 240 of lead 200, according to some embodiments, such that depressions 255 are formed directly in body 240, for example, by any suitable cutting or thermoforming process known in the art. FIG. 5 is a perspective view of a portion of fixation mechanism 250, 350, according to some alternate embodiments, wherein outermost surface 205 is formed by a tubing member 50, for example, being formed from medical grade polyurethane having a 55D durometer. Tubing member 50 is shown separate from a remainder of mechanism 250, 350, and includes depressions 255 formed therein. FIG. 5 illustrates a lumen 504 of tubing member 50, which may be sized so that tubing member 50 fits snuggly around insulation body 240 of lead 200. Depressions 255 may, or may not, extend through to lumen 504, and may be formed by any suitable cutting or thermoforming process known in the art. According to some exemplary embodiments, each depression may be about 0.05 inch wide and about 0.028 inch deep. FIG. 5 further illustrates adjacent depressions 255 being circumferentially offset from one another by an angle CO (e.g., about 120 degrees), which may preserve a structural integrity of tubing member 50. Depressions 255 formed directly in insulation body 240 may be similarly offset from one another; but in either case, depressions 255 may extend 360 degrees around insulation body 240, for example, being thermally formed. In some embodiments, tubing member 50 may extend from connector 210 to electrode 230 and have an outer diameter that is about the same as an outer diameter of electrode 230, in which case, the uniformly spaced depressions 255 extend only along a portion of the entire length of tubing member 50, for example, along about four inches of the entire length.

Figure 6:
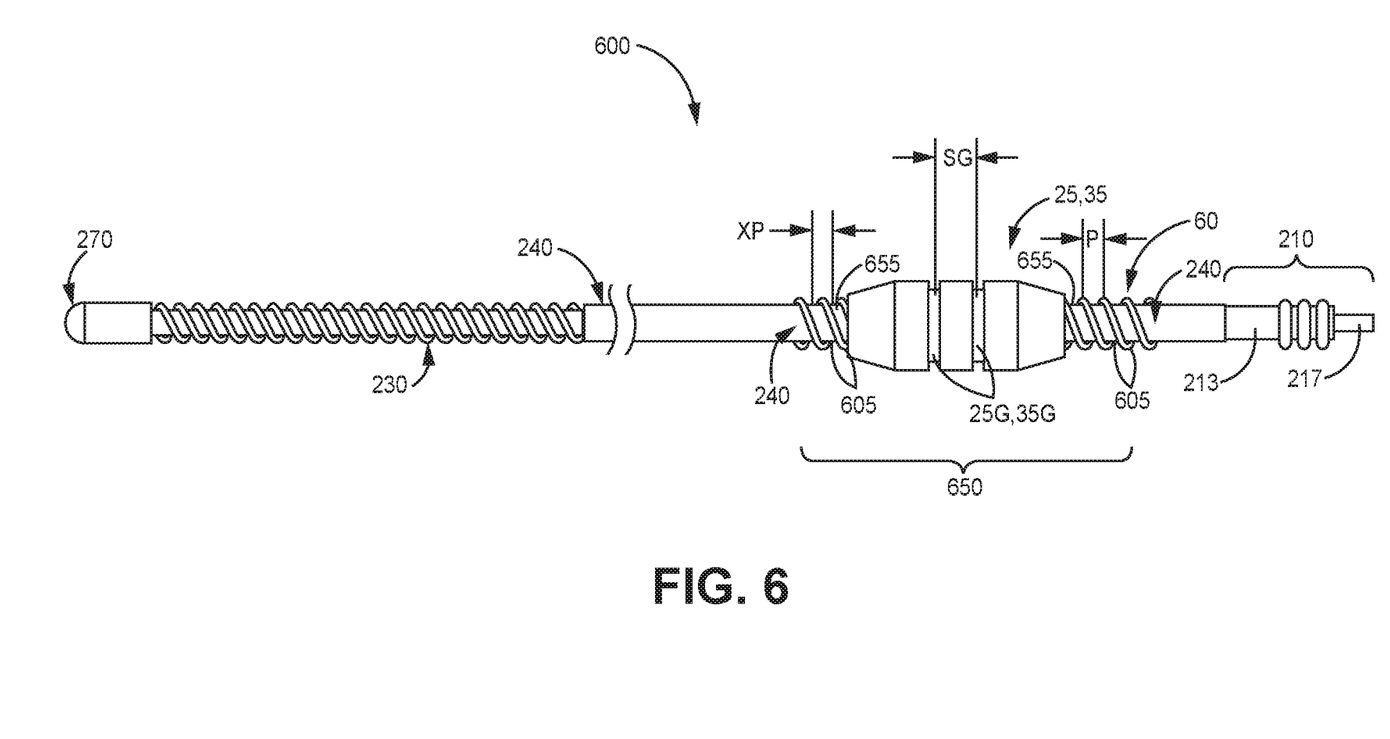
FIG. 6 is a plan view of an implantable medical electrical lead, according to some alternate embodiments.

FIG. 6 is a plan view of an implantable medical electrical lead 600 that includes a fixation mechanism 650, according to some alternate embodiments. Lead 600, like lead 200 (FIG. 2A), is shown including electrodes 230, 270, connector 210, and insulation body 240 extending therebetween. FIG. 6 illustrates fixation mechanism 650 of lead 600 including an outermost surface 605 formed by a coiled member 60, overlying insulation body 240, and portions of body 240 that are exposed between turns of coiled member 60. FIG. 6 further illustrates sleeve 25, 35 mounted around outermost surface 605, wherein sleeve internal surface 25I, 35I is in sliding engagement therewith. According to the illustrated embodiment, a plurality of depressions 655 of outermost surface 605 are defined by a pitch P of coiled member 60, which is constant along a length of coiled member 60, and may be about 0.11 inch in some embodiments. Thus, depressions 655, like depressions 255 of fixation mechanism 250, 350, are uniformly sized, and have a uniform longitudinal center-to-center spacing XP. Coiled member 60 may be formed from a wire of any suitable biocompatible material, either metal or polymer, for example, that has a diameter of about 0.017 inch in some embodiments.

With further reference to FIG. 6, as with fixation mechanism 250, 350, longitudinal center-to-center spacing SG between adjacent grooves 25G, 35G of sleeve 25, 35 is substantially the same as spacing XP, or a multiple thereof. Thus, when sutures are tightened down around sleeve 25 in grooves 25G, sleeve 25 is deformed into interlocking engagement with underlying depressions 655 in a similar fashion to that described above in conjunction with FIG. 2C. And, when sutures are tightened down around sleeve 35 in grooves 35G, each underlying ridge $35R_a$ is forced into interlocking engagement with the corresponding depression 655, as described above in conjunction with FIG. 3.

Figure 7:
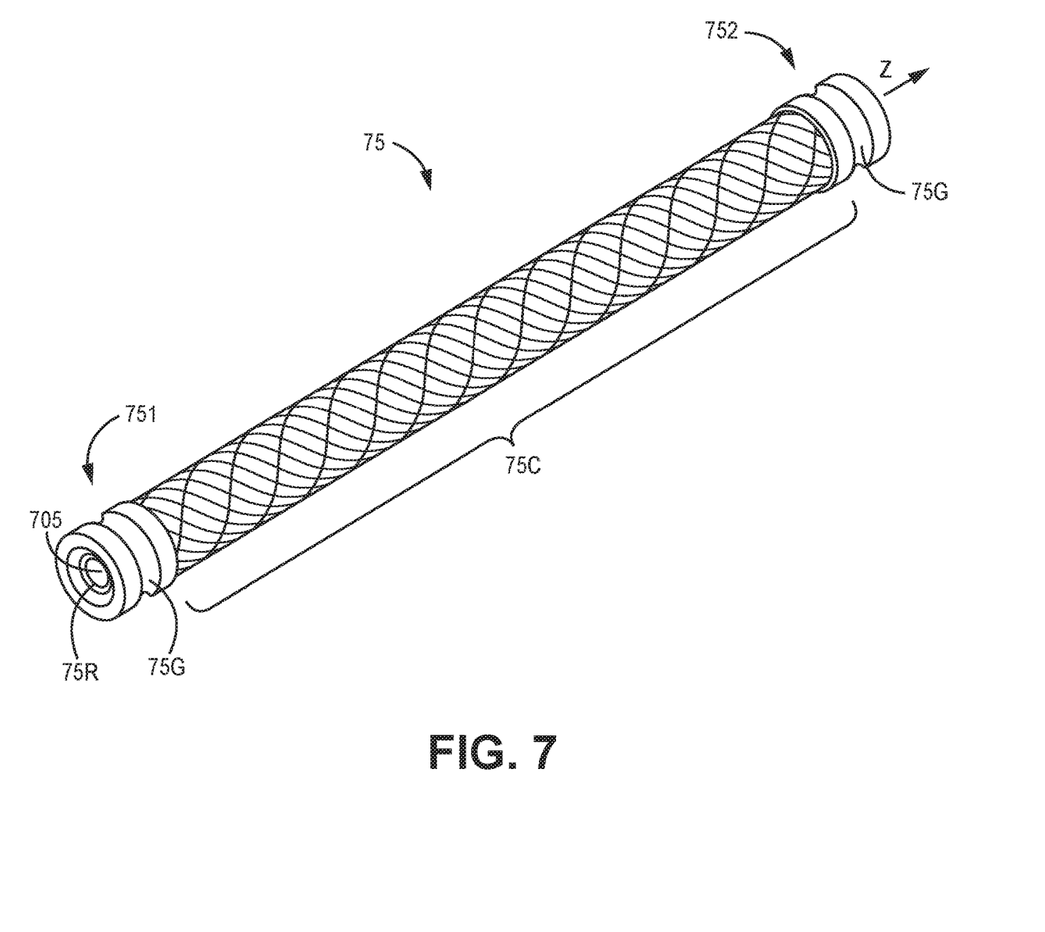
FIG. 7 is a perspective view of a sleeve which may be employed in lieu of the above-described sleeves, according to some additional embodiments.

FIG. 7 is a perspective view of a sleeve 75 which may be employed in lieu of any of the above-described sleeves, with either of outermost surfaces 205, 605, to form a fixation mechanism, according to some additional embodiments. FIG. 7 illustrates sleeve 75 including a first end 751, a second end 752, and a contractible segment 75C extending therebetween, wherein an internal surface of first and second ends 751, 752 and segment 75C define a lumen 705 of sleeve 75. FIG. 7 further illustrates each end 751, 752 including an external surface in which a suture groove 75G is formed. Each end 751, 752 further includes a ridge 75R protruding from the internal surface thereof, wherein each ridge 75R is longitudinally aligned with the corresponding groove 75G and is sized to fit within any one of depressions 255, 655 of outermost surface 205, 605. According to some embodiments and methods, when sleeve 75 is mounted around outermost surface 205, 605, the internal surface along an entire length of sleeve 75 is in sliding engagement with outermost surface 205, 605, until an operator aligns ridge 75R with one of depressions 255, 655, tightens a suture around first end 751 in groove 75G so that ridge 75R comes into interlocking engagement with depression 255, 655, and then pulls second end 752 away from first end 751, per arrow Z, to cause contractible segment 75C to constrict around insulation body 240. After pulling second end 752, the operator may tighten another suture around second end 752 to complete fixation of lead 200, 600. In some embodiments, the tightened sutures may only secure sleeve 75 to insulation body 240, and sleeve segment 75C includes micro-barbs/hooks that engage with surrounding tissue to complete the fixation of lead 200, 600, for example, as described for embodiments disclosed in the commonly assigned and co-pending United States patent application having the U.S. Publication No. 2015/0306374 (U.S. application Ser. No. 14/283,278 to Seifert et al.), the disclosure of which is incorporated herein by reference in its entirety.

The foregoing detailed description describes specific embodiments, however, it may be appreciated that various modifications and changes can be made without departing from the scope of the disclosure as set forth in the appended claims.

The invention claimed is:

1. An implantable medical electrical lead comprising:
   a connector;
   an electrode;
   an elongate insulation body extending between the connector and the electrode, the body surrounding a longitudinal axis;
   an elongate conductor extending within the insulation body and coupling the electrode to the connector; and
   a fixation mechanism comprising:
      an outermost surface of the lead overlaying the insulation body and surrounding the longitudinal axis, the outermost surface including a plurality of depressions spaced apart from one another along a length of the body, wherein the outermost surface of the lead surrounds one or more lumens and each depression does not extend to any of the one or more lumens, wherein each depression defines an arc having an arc center on the longitudinal axis, and wherein each depression extends around at least part of the circumference of the body; and
      a relatively flexible sleeve mounted around the outermost surface of the lead and surrounding the longitudinal axis, the sleeve comprising an internal surface, an external surface, and at least two suture grooves formed in the external surface and extending around a circumference thereof, the internal surface being in sliding engagement with the outermost surface of the lead, and a longitudinal center-to-center spacing between adjacent suture grooves being substantially the same as, or a multiple of, a longitudinal center-to-center spacing between adjacent depressions of the outermost surface of the lead, wherein the sleeve is configured to form an interlocking engagement between the internal surface of the sleeve and at least one of the depressions of the outermost surface of the lead, wherein when the sleeve is configured to form the interlocking engagement, a suture applying a constricting force around the circumference of one of the suture grooves generates a protrusion of the internal surface of the sleeve and the protrusion inserts into the depression of the outermost surface of the lead.

2. The lead of claim 1, wherein the longitudinal center-to-center spacing between each adjacent depression is uniform along the length of the body.

3. The lead of claim 1, wherein the outermost surface of the lead is a tubing member overlaying the insulation body, the plurality of depressions being formed in the tubing member.

4. The lead of claim 1, wherein the outermost surface of the lead comprises a coiled member, overlaying the insulation body, and wherein the plurality of depressions are formed by the coiled member and portions of the insulation body between turns of the coiled member.

5. The lead of claim 1, wherein a first depression extends around a first arc of the circumference of the body and a second depression extends around a second arc of the circumference of the body, and wherein the first arc has a first midpoint and the second arc has a second midpoint, and wherein the first midpoint is angularly displaced from the second midpoint around the circumference of the body.

6. The lead of claim 1, wherein the outermost portion of the lead along which the plurality of depressions are spaced apart is about four inches long.

7. The lead of claim 1 wherein each depression extends around at least one-quarter of the circumference of the body.

8. The lead of claim 1 wherein each depression is a circular depression extending 360 degrees around the body.

9. An implantable medical electrical lead comprising:
a connector,
an electrode,
an elongate insulation body extending between the connector and the electrode,
an elongate conductor extending within the insulation body and coupling the electrode to the connector, and
a fixation mechanism, the fixation mechanism comprising:
an outermost surface of the lead overlaying the insulation body, the outermost surface including a plurality of depressions spaced apart from one another along a length of the body, each depression extending around at least part of the circumference of the body, a longitudinal center-to-center spacing between each adjacent depression being uniform along the length, and each depression being of substantially the same size; and
a relatively flexible sleeve mounted around the outermost surface of the lead, the sleeve comprising an internal surface, an external surface, at least two suture grooves formed in the external surface and extending around a circumference thereof, and at least two ridges protruding from the internal surface, the internal surface being in sliding engagement with the outermost surface of the lead, each ridge being sized to fit within one of the depressions of the outermost surface of the lead, and each ridge being longitudinally aligned with a corresponding suture groove.

10. The lead of claim 9, wherein a longitudinal center-to-center spacing between adjacent suture grooves of the sleeve of the fixation mechanism is substantially the same as, or a multiple of, the longitudinal center-to-center spacing between adjacent depressions of the outermost surface of the lead.

11. The lead of claim 9, wherein a profile defined by the internal surface of the sleeve of the fixation mechanism is generally elliptically shaped.

12. The lead of claim 11, wherein the internal surface of the sleeve includes a flat aspect, from which the ridges protrude.

13. The lead of claim 9, wherein the outermost surface of the lead comprises a tubing member overlaying the insulation body, the plurality of depressions being formed in the tubing member.

14. The lead of claim 9, wherein the outermost surface of the lead comprises a coiled member, overlaying the insulation body, and wherein the plurality of depressions are formed by the coiled member and portions of the insulation body between turns of the coiled member.

15. The lead of claim 9, wherein each depression of the outermost surface does not extend all the way around a circumference of the insulation body, and adjacent depressions are circumferentially offset from one another.

16. The lead of claim 9, wherein the length of the insulation body, along which the plurality of depressions are spaced apart, is about four inches long.

17. The lead of claim 9, wherein:
the sleeve of the fixation mechanism further comprises a contractible segment extending between a first end of the sleeve and a second end of the sleeve, the contractible segment constricting around the insulation body when the second end is pulled longitudinally away from the first end;
the internal and external surfaces of the sleeve are divided between the first and second ends of the sleeve;
a first of the at least two suture grooves and a first of the at least two ridges are located at the first end of the sleeve; and
a second of the at least two suture grooves and a second of the at least two ridges are located at the second end of the sleeve.

18. An implantable medical electrical lead comprising:
a connector;
an electrode;
an elongate insulation body extending between the connector and the electrode, the insulation body including an outermost surface integral with the insulation body and the outermost surface including a plurality of depressions extending around at least a portion of the circumference of the insulation body, wherein the outermost surface of the insulation body surrounds one or more lumens and the plurality of depressions does not extend to any of the one or more lumens;
an elongate conductor extending within the insulation body and coupling the electrode to the connector; and
a relatively flexible sleeve mounted around the outermost surface of the insulation body and the plurality of depressions, the sleeve comprising an internal surface, an external surface, and at least one suture groove formed in the external surface and extending around a circumference of the sleeve, the internal surface configured to be moveable with respect to the outermost surface of the insulation body before sutured using the suture groove and configured to engage with at least one depression of the plurality of depressions of the outermost surface of the insulation body when sutured using the suture groove such that the internal surface of the sleeve is fixated with respect to the outermost surface of the insulation body by the interaction of the internal surface of the sleeve and the at least one depression of the outermost surface of the insulation body.

19. An implantable medical electrical lead comprising:
a connector;

an electrode;

an elongate insulation body extending between the connector and the electrode;

an elongate conductor extending within the insulation body and coupling the electrode to the connector; and a fixation mechanism comprising:

an outermost surface of the lead overlaying the insulation body, the outermost surface including a plurality of depressions spaced apart from one another along a length of the body, each depression extending around at least part of the circumference of the body; and a relatively flexible sleeve mounted around the outermost surface of the lead, the sleeve comprising an internal surface, an external surface, and at least two suture grooves formed in the external surface and extending around a circumference thereof, the internal surface being in sliding engagement with the outermost surface of the lead, and a longitudinal center-to-center spacing between adjacent suture grooves being substantially the same as, or a multiple of, a longitudinal center-to-center spacing between adjacent depressions of the outermost surface of the lead, wherein the sleeve further comprises a ridge protruding from the internal surface, the ridge being sized to fit within one of the plurality of depressions of the outermost surface of the lead.

20. The lead of claim 19, wherein the ridge is longitudinally aligned with one of the suture grooves.

21. The lead of claim 19, wherein the ridge is longitudinally spaced apart from the suture grooves, a spacing between the ridge and a closest one of the suture grooves being substantially the same as the longitudinal center-to-center spacing between the suture grooves.

22. The lead of claim 19, wherein a profile defined by the internal surface of the sleeve is elliptically shaped, the internal surface of the sleeve includes a flat aspect, and the ridge protrudes from the flat aspect.

23. The lead of claim 22, wherein the sleeve is configured such that deformation of the sleeve disengages the ridge from the one of the plurality of depressions.

* * * * *